US006442230B1

(12) United States Patent
Wilting et al.

(10) Patent No.: US 6,442,230 B1
(45) Date of Patent: Aug. 27, 2002

(54) COMPUTED TOMOGRAPHY DEVICE INCLUDING A POSITION MEASURING SYSTEM

(75) Inventors: Jantje E. Wilting, Heemskerk (NL); Roland Proksa, Hamburg (DE); John A. M. Verbruggen, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/527,199

(22) Filed: Mar. 16, 2000

(30) Foreign Application Priority Data

Mar. 17, 1999 (EP) .............................. 99200813

(51) Int. Cl.⁷ ................................ A61B 6/00
(52) U.S. Cl. .................... 378/20; 378/205; 600/429
(58) Field of Search .................... 378/65, 204, 205, 378/4, 20; 600/429

(56) References Cited

U.S. PATENT DOCUMENTS

| 4,385,397 A | * | 5/1983 | Verro ............................ 378/20 |
| 5,622,187 A | * | 4/1997 | Carol ........................... 128/897 |
| 6,035,228 A | * | 3/2000 | Yanof et al. ................ 600/429 |
| 6,032,066 A | * | 12/2000 | Lu et al. ..................... 600/407 |

OTHER PUBLICATIONS

"Interactive Freehand Targeting with Real.–Time Visual Feedback in Whole Body Computed Tomography Guided Radiological Intervention" by B. Baumann, et al. in Computer Assisted Radiology, 1996 Elsevier Science BV. pp. 699–704.
"Visually Interactive Navigation in Interventional Radilogy" by Augustinus L. Jacob et al., in International Society for Computer Aided Surgery, in vol. 3., No. 2, Dec. 1996, 71–71.
"Interactive Single–Step Frameless Freehand Navigation in Iliosacral Screw Fixation of Sacral Fractures and Fracture Dislocations" by Al Jacob et al., in Computer Assisted Orthopedic Surgery, 1999, pp. 147–152.

* cited by examiner

Primary Examiner—David P. Porta
Assistant Examiner—Therese Barber
(74) Attorney, Agent, or Firm—John Vodopia

(57) ABSTRACT

A computed tomography system includes a gantry provided with an examination opening. The computed tomography system is provided with a position measuring system for measuring the position of the gantry. Preferably, an optical position measuring system which includes a camera unit is employed. The camera unit is suspended from a suspension point above the gantry.

7 Claims, 1 Drawing Sheet

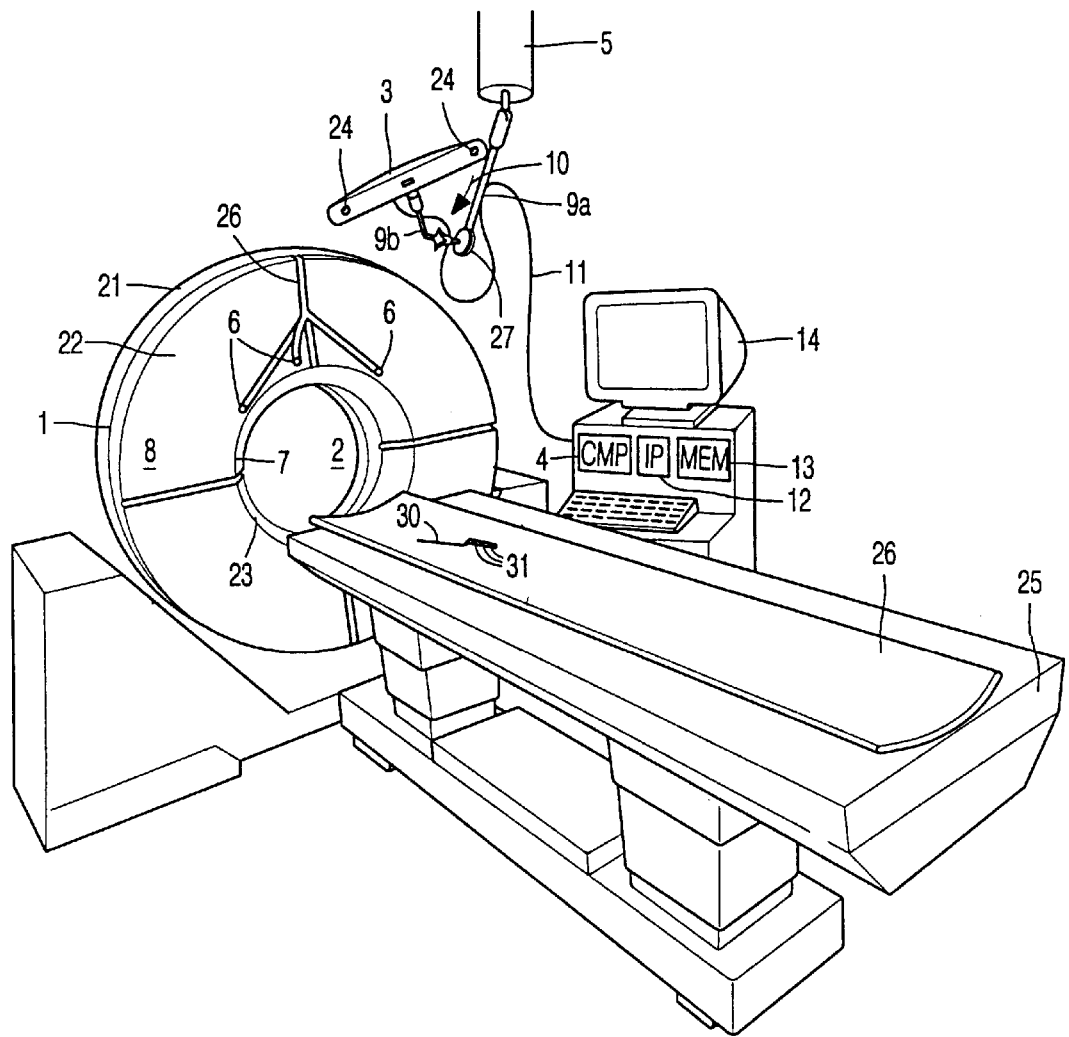

COMPUTED TOMOGRAPHY DEVICE INCLUDING A POSITION MEASURING SYSTEM

BACKGROUND OF THE INVENTION

1. Field of the Invention

The invention relates to a computed tomography device which includes a gantry provided with an examination opening, a position measuring system for measuring the position of the gantry.

2. Description of Related Art

A computed tomography device of this kind is described in European patent application No. 98202074.5.

The patient to be examined is accommodated on an examination table. During the examination the patient on the examination table is moved partly into the examination opening of the computed tomography device. The computed tomography device includes an X-ray source for irradiating the patient to be examined by means of X-rays from different directions. The computed tomography device also includes an X-ray detector for the detection of X-rays, having traversed the patient, from different directions. The X-ray source then irradiates the patient from different directions and the X-ray detector picks up density profiles of the patient for the various directions. A reconstruction unit extracts slice images of the patient from the density profiles.

During the examination the physician introduces a surgical or interventional instrument, such as biopsy needle, into the body of the patient. The surgical instrument is provided with transmission elements such as diodes emitting light or infrared radiation (LEDs or IREDs). The cited European patent application describes a computed tomography device which includes a position measuring system with a camera unit mounted on a mast. The position measuring system comprises the camera unit and a computer. The computer is connected to the camera unit so that the camera unit can supply the computer with image signals. The camera unit picks up images of the transmission elements on the surgical instrument from different directions and a computer computes the position of the surgical instrument relative to the camera unit from said images. Furthermore, transmission elements, for example LEDs or IREDs again, are also provided on the gantry of the computed tomography device. The camera unit also picks up images of the transmission elements on the gantry and the computer computes the position of the gantry relative to the camera unit from these images. The position of the gantry is related directly to the position of the cross-section of the patient of which a slice image is formed in the relevant position of the gantry. It has been found that the relationship between the gantry positions measured by the camera unit and the position of the cross-section of the patient which is imaged in the slice image can be accurately calibrated. The transformation of positions in said cross-section to corresponding positions in the slice image can be derived from the calibrated relationship between the position of the gantry and the position of the cross-section of the patient imaged in this position of the gantry. On the basis of the positions, measured by the camera unit, of on the one hand the surgical instrument and on the other hand the position of the gantry, also measured by the camera unit, and the position, derived therefrom, of the cross-section of the patient which is reproduced in the slice image, it is possible to reproduce, using the transformation, also the corresponding position of the surgical instrument in the rendition of the slice image. The physician, for example a surgeon or radiological interventionist, can thus track the surgical instrument within the body of the patient in the image without having a direct view of the instrument.

The computed tomography device described in the cited European patent application is provided with a position measuring system with a camera unit which is mounted on a mast. The mast is connected to the examination table. It is a drawback of the described computed tomography device that the mast could interfere with the accessibility of the patient during the examination. Moreover, it may occur that the physician stands between the camera unit and the gantry during the examination, so that the light or infrared radiation emitted by the transmission elements on the gantry is intercepted by the physician. The determination of the position of the gantry by the camera unit could thus unintentionally be interrupted.

Citation of a reference herein, or throughout this specification, is not to be construed as an admission that such reference is prior art to the Applicant's invention of the invention subsequently claimed.

SUMMARY OF THE INVENTION

It is an object of the invention to provide a computed tomography device which is provided with a position measuring system and in which the camera unit of the position measuring system practically does not interfere with the execution of the examination.

This object is achieved by means of a computed tomography device according to the invention in which the camera unit is suspended from a suspension point situated above the examination opening.

The camera unit is suspended from a suspension point which is situated above the examination opening, i.e. the suspension point is situated at a level above the floor of the space in which the computed tomography device is accommodated which is higher than the level of the examination opening above the floor. This is achieved, for example by situating the suspension point above the gantry, i.e. at a greater height above the floor. The camera unit itself can be arranged in various positions; for example, the camera unit is situated at a level which is higher than that of the gantry, or at a level which is higher than that of the examination opening, or at a level which is higher than the center or higher than the lower side of the examination opening. Because the camera unit is suspended from a suspension point above the examination opening of the computed tomography device, for example from the ceiling of the examination room in which the computed tomography device is installed, the mast can be dispensed with. Because of the absence of a mast, the accessibility of the patient during the examination is enhanced. As the camera unit is suspended above the computed tomography device, moreover, (unintentional) blocking of the line of sight between the camera unit and the gantry, notably the transmission elements on the gantry, by the physician during the treatment is avoided.

Most commercially available camera units which are suitable for use in conjunction with a computed tomography device in order to measure the positions of the surgical instrument and of the gantry have a sensitivity range which is comparatively small; the sensitivity range of inexpensive camera units amounts to approximately one cubic meter. The sensitivity range of the camera unit is to be understood to mean that part of the space in which the camera unit picks up images of the emitter elements which are sufficiently accurate so as to enable the extraction of reliable results concerning the positions of these emitter elements. Generally speaking, the examination opening of the computed tomography device is shaped more or less as a cylindrical tunnel. For example, the tunnel has a width of between 40 cm and 90 cm and also a length of from approximately 40 cm to 90 cm. It has been found that when the camera unit is suspended above the examination opening and in front of one of the tunnel entrances, practically the entire interior of the tunnel will remain within the sensitivity range of the camera unit. This enables the use of a comparatively inexpensive camera unit, accurate results concerning the position of the surgical instrument being obtained nevertheless.

It also has been found that the angle of aperture of the camera unit can be readily adjusted to the operating zone in which the surgical instrument is moved. The angle of aperture of the camera unit is the range of directions wherefrom the camera unit can accurately pick up images of the transmission elements on the gantry and on the surgical instrument.

When the transmission elements on the gantry are arranged near the entrance of the tunnel, the transmission elements on the gantry can also be kept within the sensitivity range of the camera unit which views the tunnel from above. The transmission elements are then mounted preferably on the edge of the tunnel entrance. A camera unit having a comparatively small sensitivity range of approximately one cubic meter can thus keep a suitable view of the transmission elements on the gantry as well as of the transmission elements on the surgical instrument, even when the surgical instrument is manoeuvred within the body of the patient in the tunnel. In the case of complex medical operations, new slice images are picked up during the intervention. The part of the body of the patient to be operated must then remain in the tunnel-shaped examination opening of the computed tomography device and the surgical instrument is also moved inside the tunnel. The invention enables the use of a comparatively simple, inexpensive camera unit even for such complex operations. It is notably possible to keep the transmission elements on the gantry, and the transmission elements on the surgical instrument in sight of the camera unit even when the part of the patient to be examined and the surgical instrument are situated further in the tunnel of the examination opening.

The gantry of the computed tomography device is shaped more or less as a ring or a torus. The tunnel-like examination opening is recessed at the center of the torus. The X-ray source and the X-ray detector are suspended in the gantry and can rotate about the patient together. In order to form the density profiles of the patient, the X-ray source and the X-ray detector rotate inside the ring about the patient, the opening enclosed by the ring being the examination space. The gantry is covered with cover plates. Part of the cover plates extends transversely of the axis of the tunnel and constitutes the front surface of the gantry. The camera unit and the computed tomography device are arranged relative to one another in such a manner that the front surface of the gantry faces the camera unit. The transmission elements for the gantry are preferably mounted on said front surface. On the cover plates of the front surface there is adequate space to accommodate the transmission elements themselves and the necessary electrical wiring for the transmission elements. Moreover, the camera unit has good sight of the transmission elements on the front surface; this is notably so when the transmission elements are arranged on the front surface at the edge of the tunnel entrance, i.e. at the edge which is formed by the transition from the interior of the tunnel to the cover plate (plates) of the front surface.

Moreover, the camera unit is preferably suspended by way of a pivot arm. The pivot arm includes two or more sections which are pivotable relative to one another. One end of the pivot arm is secured to the suspension point and the camera unit is mounted at its other end. The suspension point is situated above the entrance of the tunnel in the gantry; for example, the suspension point is provided on the ceiling of the room in which the computed tomography device is installed. Because the pivot arm includes a plurality of mutually independently pivotable sections, the camera unit can be readily moved to a desired position in which it has optimum sight of the transmission elements on the gantry and preferably also of the transmission elements on the surgical instrument, even when the surgical instrument is moved inside the tunnel-shaped examination opening. Moreover, the pivot arm enables the camera unit to be swung away quickly if more room is required above the body of the patient to be examined, for example when additional equipment for treatment of the patient is moved in.

BRIEF DESCRIPTION OF THE DRAWINGS

These and other aspects of the invention are apparent from and will be elucidated, by way of non-limitative example, with reference to the embodiment described hereinafter and shown in the accompanying drawing.

The FIGURE is a diagrammatic representation of a computed tomography device according to the invention which is installed in a room for radiology.

DETAILED DESCRIPTION OF THE PREFERRED EMBODIMENT

The FIGURE is a diagrammatic representation of a computed tomography device according to the invention as it is installed in a room for radiology. The computed tomography device includes a gantry 1 in which the X-ray source and the X-ray detector are suspended. The X-ray source and the X-ray detector are not visible in the Figure, because the gantry 1 is covered with cover plates 21, 22, 23. The gantry 1 is shaped as a ring or a torus which encloses the examination opening 2. The examination opening is shaped as a tunnel having a length of approximately 60 cm and a width of approximately 60 cm. The patient on the patient table 25 is moved partly into the tunnel 2 during examination or treatment of the patient. The computed tomography device according to the invention is provided with a position measuring system which includes the camera unit 3 with the computer 4. The camera unit is suspended from a suspension point 5 which is situated above and in front of the gantry 1 of the computed tomography device. In the present embodiment the suspension point 5, whereto the camera unit is secured by way of the pivot arm 10, is situated above the examination table 25. It is also possible to situate the suspension point above, i.e. at a level higher than that of the table top 26, the floor and adjacent the examination table 25. The camera unit 3 can be moved to the desired position by way of the pivot arm 10; in this respect it is not very important where exactly the suspension point 5 is situated above the examination table 25, for as long as the suspension point 5 is situated at a level above the floor which is higher than that of the table top 26. The camera unit in the present embodiment is provided with two CCD image sensors 24. The transmission elements 6, preferably LEDs or IREDs, are mounted on the gantry 1. As is shown in the Figure, the transmission elements 6 are preferably provided at the edge 7 of the entrance of the tunnel 2. Particularly suitable positions for the transmission elements are situated on the parts of the cover plate 22 which constitutes the front surface 8 of the gantry. This front surface 8 is formed by the part of the cover plate 22 which extends essentially perpendicularly to the longitudinal axis of the tunnel 2. Electric cables 26 in the present embodiment serve to supply electric power to the transmission elements and are arranged on the exterior of the cover plates. Evidently, the electric power can also be applied to the transmission elements 6 by way of electric cables hidden behind the cover plates 21, 22 of the gantry 1.

The camera unit 3 is connected to the suspension point 5 by way of the pivot arm 10. The pivot arm includes, for example two sections 9a, 9b which are connected to the pivot 27 so as to be rotatable relative to one another. Moreover, one section 9a of the pivot arm is rotatably connected to the suspension point 5 by way of a ball joint 28. The camera unit 3 is connected to the other section 9b of the pivot arm in such a manner that the camera unit is capable of rotation about the axis of the section 9b. Because of this suspension of the camera unit 3, the camera unit 3 will not be in the way during the interventional treatment but nevertheless keeps suitable sight of the transmission elements 6 on the gantry.

The camera unit is connected to the computer 4 by way of a data cable 11. The image signals of the camera unit 3, representing the images of the transmission elements 6 on the gantry 1 and of the transmission elements 31 on the surgical instrument 30, are applied to the computer 4 via the data cable 11. The computer computes the positions of the gantry and of the surgical instrument on the basis of the image signals of the camera unit. Based on the calibration performed in advance, the computer also computes, using the computed position of the gantry, the position of the cross-section of the patient to be examined which is to be imaged as a slice image. The results of this calculation are applied to the image processing unit 12. The slice image is reconstructed, via a reconstruction unit which is included in a computed tomography device and while utilizing inter alia an inverse Radon transformation, from the density profiles picked up by the X-ray detector. The image information of the slice image is stored, for example in the form of a matrix of brightness values, in an image memory 13 and is applied to the image processing unit 12. From the computed positions of the cross-section of the patient reproduced in the slice image, the computed position of the surgical instrument, and the image information of the slice image, the image processing unit derives an image signal which represents the slice image in which the current position of the surgical instrument is reproduced. The image processing unit 12 is connected to the monitor 14 in order to supply the monitor with the image signal derived by the image processing unit 12. The slice image of the patient, also showing the current position of the surgical instrument 30, can thus be displayed on the monitor 14.

All references cited herein, as well as the priority document European Patent Application 99200813.6 filed Mar. 17, 1999, are incorporated herein by reference in their entirety and for all purposes to the same extent as if each individual publication or patent or patent application was specifically and individually indicated to be incorporated by reference in its entirety for all purposes.

What is claimed is:

1. A computed tomography device comprising:

a gantry provided with an examination opening, a position measuring system for measuring the position of the gantry, wherein the position measuring system includes a camera unit for receiving position measuring signals emitted directly from a fixed position relative the examination opening, and wherein the camera unit is suspended from a suspension point situated above the examination opening.

2. A computed tomography device as claimed in claim 1 wherein the examination opening is shaped as a tunnel and wherein the suspension point is situated above the examination opening and in front of an entrance of the tunnel.

3. A computed tomography device as claimed in claim 1 wherein the examination opening is shaped as a tunnel, and further comprising transmission elements which are mounted on the gantry in order to emit signals whereto the camera unit is sensitive, the transmission elements being mounted on the gantry at the edge of the tunnel entrance.

4. A computed tomography device as claimed in claim 3 wherein the gantry further comprises a front surface which extends transversely to the axis of the tunnel, and wherein the transmission elements are mounted at an area of transition between the front surface and the interior wall of the tunnel.

5. A computed tomography device as claimed in claim 1 further comprising a pivot arm which includes a plurality of mutually pivotable sections and wherein the camera unit is secured to the suspension point by means of the pivot arm.

6. The computed tomography device as claimed in claim 2 further comprising transmission elements which are mounted on the gantry in order to emit signals whereto the camera unit is sensitive, the transmission elements being mounted on the gantry at the edge of the tunnel entrance.

7. The computed tomography device as claimed in claim 6 wherein the gantry further comprises a front surface which extends transversely to the axis of the tunnel, and wherein the transmission elements are mounted at an area of the transition between the front surface and the interior wall of the tunnel.

* * * * *